United States Patent

Nakajima et al.

Patent Number: 5,338,761
Date of Patent: Aug. 16, 1994

[54] EMULSIFIED COMPOSITION

[75] Inventors: Hideo Nakajima; Miyuki Kohchi; Satoshi Tomomasa, all of Yokohama, Japan

[73] Assignee: Shiseido Company Ltd., Tokyo, Japan

[21] Appl. No.: 413,940

[22] Filed: Sep. 28, 1989

[30] Foreign Application Priority Data

Sep. 29, 1988 [JP] Japan .................. 63-245120

[51] Int. Cl.$^5$ .............................. A61K 47/00
[52] U.S. Cl. ................... 514/772; 514/786; 514/937
[58] Field of Search .................. 514/772, 786, 937

[56] References Cited

U.S. PATENT DOCUMENTS

| | | | |
|---|---|---|---|
| 4,280,996 | 7/1981 | Okamoto et al. | 514/78 |
| 4,323,563 | 4/1982 | Takami et al. | 514/78 |
| 4,677,099 | 6/1987 | Shinitzky et al. | 514/78 |
| 4,784,845 | 11/1988 | Desai et al. | 514/943 |
| 4,801,455 | 1/1989 | List et al. | 514/937 |
| 4,816,247 | 3/1989 | Desai et al. | 514/938 |

*Primary Examiner*—Frederick E. Waddell
*Assistant Examiner*—Kimberly R. Jordan
*Attorney, Agent, or Firm*—Sprung Horn Kramer & Woods

[57] ABSTRACT

An emulsified composition having an average particle size of 0.010 to 0.070 μm contains at least the following components (A), (B) and (C):

(A) a lipid-soluble drug and a lipid;
(B) glycerol and water;
(C) a phospholipid and/or a water-soluble nonionic surfactant having a molecular weight of 1000 or more, with (A)/(C) being 0.5 to 5 (weight ratio).

6 Claims, 3 Drawing Sheets

EMULSIFIED COMPOSITION

BACKGROUND OF THE INVENTION

1. Field of the Invention

The present invention relates to an emulsified composition. More specifically, it relates to an emulsified composition suitable for use as a preparation for parenteral administration.

2. Description of the Related Art

Various emulsified compositions have been used in the field of, for example, pharmaceutical preparations and quasi-drug. For example, a fat emulsion for intravenous injection, which is a dispersion of lipid spheres with an average particle size of about 0.2 μm dispersed in an aqueous phase, is already known in the art. This emulsion is usually formed by emulsifying a vegetable oil with lecithin as the emulsifier, using a high pressure homogenizer, and is utilized for a nutrient supplementation of patients or as the preparation for a parenteral administration of a lipid-soluble drug. Particularly, it is effective as the preparation for an intravenous injection of a lipid-soluble drug, which usually cannot be intravenously injected as an aqueous solution, and is utilized as a drug delivery system.

Recently, passive or active oriented drug delivery systems using microspheres have been studied, it has been found that particles of 0.100 to 2.000 μm, when administered intravenously, intraarterially or intraperitoneally, are rapidly taken in from the blood stream by macrophages of the reticuloendothelial system, to become localized in lysosomes of Kupffer cells of the liver, and that particles of 0.050 μm or less are considered to permeate through the liver endothelial system and accumulate at tumor tissues (Pharmacy International 2 (3) 1984). From such a standpoint, the above lipid emulsion for an intravenous injection with an average particle size of 0.2 μm, which has a particle size readily taken into the reticuloendothelial system, particularly the liver, is not satisfactory as the preparation for a parenteral administration of a lipid-soluble drug, and therefore, it is very important in pharmaceutical preparation to be able to prepare particles of 0.050 μm or less which can be parenterally administered. The above-mentioned lipid emulsion for intravenous administration is known as an emulsion which can be parenterally administered, but in the system of this lipid emulsion, it is very difficult to prepare particles of 0.050 μm or less which can be parenterally administered, namely nano-lipid spheres, and thus further research must be made into this problem.

SUMMARY OF THE INVENTION

Accordingly, the objects of the present invention are to eliminate the above-mentioned disadvantages of the prior art and to provide a stable emulsified composition in which lipid spheres having an average particle size of 0.010 to 0.070 μm are dispersed in an aqueous phase.

Other objects and advantages of the present invention will be apparent from the following description.

In accordance with the present invention, there is provided an emulsified composition having an average particle size of 0.010 to 0.070 μm comprising at least the following components (A), (B) and (C):

(A) a lipid-soluble drug and a lipid;
(B) glycerol and water;
(C) a phospholipid and/or a water-soluble nonionic surfactant having a molecular weight of 1000 or more, with (A)/(C) being 0.5 to 5 (weight ratio).

Preferably, the weight ratio of glycerol/water during emulsification is 3/7 to 9/1.

The average particle sizes used herein are all measured by the dynamic light scattering method, specifically by a NICOMP-270 (manufactured by HIAC/ROYCO).

BRIEF DESCRIPTION OF THE DRAWINGS

The present invention will be better understood from the description set forth below with reference to the accompanying drawings, wherein.

DESCRIPTION OF THE PREFERRED EMBODIMENTS

Figure 1:
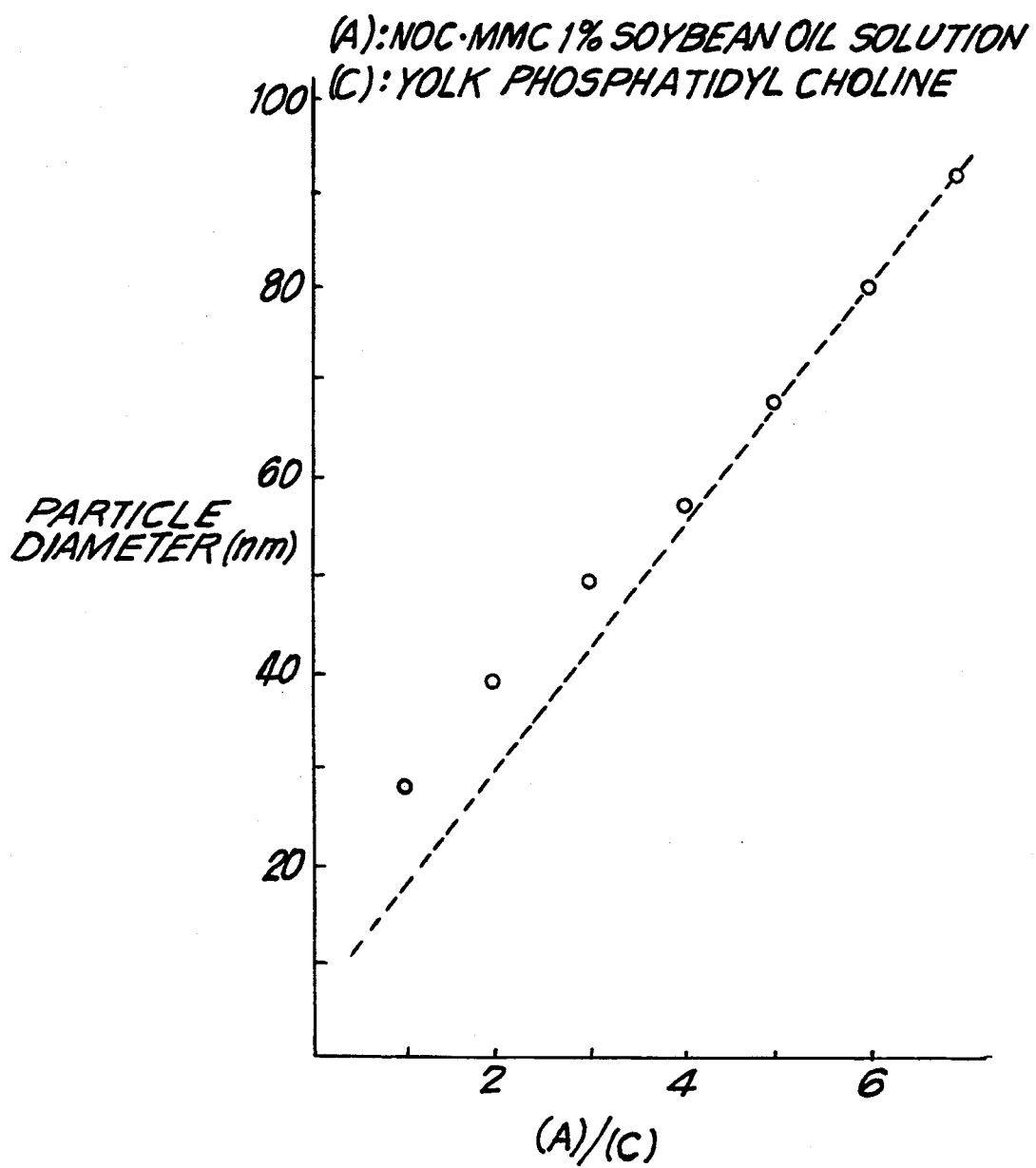
FIG. 1 shows a correlation between a particle diameter and a ratio (A)/(C) when a phospholipid is used as a component (C)

The lipid usable in the present invention may include vegetable oils such as soybean oil, corn oil, safflower oil, cottonseed oil, and coconut oil; synthetic or semi-synthetic mono-, di-, tri-glycerides; sterols such as cholesterol and chenodeoxycholic acid; cholesterol esters such as cholesteryl linoleate and cholesteryl caprylate; and monoesters such as oleyl oleate, ethyl linoleate, and ethyl laurate. These lipids may be used alone or in any combination thereof.

Generally speaking, the smaller the number of carbon atoms of the lipid, the easier it is to dissolve the drug but the emulsion stability becomes poor. For this reason, when a mono-, di-, tri-glyceride having 33 or less carbon atoms is used, or when a monoester having 22 or less carbon atoms is used, it becomes necessary to contain a triglyceride having a number of carbon atoms of 45 or a monoester having a number of carbon atoms of 26 or more in an amount of 1% or more in the lipid. This is because, if the emulsified composition is prepared by using a mono-, di-, tri-glyceride having a number of carbon atom of 33 or less or a monoester having a number of carbon atoms of 22 or less, the stability thereof with a lapse of time is poor, and thus the particle size becomes larger.

The lipid-soluble drug usable in the present invention may be any drug which can be dissolved in the above lipid, as exemplified by antitumor agents such as mitomycin, bleomycin, docsorbicin, hexamethylmelamine, futrafur oleic acid ester, and dilauric acid ester of 5-FU; antibacterial and antifungal agents such as penicillin, erythromycin, cephalosporin, streptomycin, kanamycin, tetracycline, chloramphenicol, isoniazide, cycloserine, amphoterin B, and glyceofurbin; non-steroidal antiphogistics such as salicylate, indomethacin, aminopirin, phenacetin, ibuprofen, frulubibrofen, ketoprofen, and diclofenac; hormone agents such as prostaglandins, and synthetic steroid; immune controllers such as cyclosporin; and lipid-soluble vitamins such as vitamin A, vitamin D, and vitamin E.

Although there are no critical limitations to the content of the lipid-soluble drug in the component (A), the lipid-soluble drug may be preferably $1 \times 10^{-6}\%$ to 99.9% by weight, preferably $1 \times 10^{-5}\%$ to 99.5% by weight.

The phospholipid and the water-soluble nonionic surfactant with a molecular weight of 1000 or more in the present invention function as the emulsifiers.

The phospholipid usable in the present invention may include lecithin derived from yolk lecithin, soybean lecithin, hydrogenated products thereof, phosphatidyl choline, phosphatidylethanolamine, phosphatidyl inositol, phosphatidylserine, sphingomyelin, phosphatidicacid, and phytoglycolipid, which are synthesized or separated and purified from natural products. Examples of the nonionic surfactants are polyoxyethylene (hereinafter called POE) sorbitane fatty acid esters such as POE sorbitane monooleate, POE sorbitane monostearate, and POE sorbitane trioleate; POE sorbitol fatty acid esters such as POE sorbitol monooleate, POE sorbitol pentaoleate, and POE sorbitol monstearate; POE glycerine fatty acid esters such as POE glycerol monostearate; POE fatty acid esters such as POE monooleate, POE distearate, and POE dioleate; POE alkyl ethers such as POE oleyl ether, POE stearyl ether, and POE behenyl ether; POE sterol ethers such as POE cholestanol ether and POE cholesterol ether; POE-POP block polymers; POE-POP alkyl ethers such as POE-POP cetyl ether; POE castor oil or hydrogenated oil derivatives such as POE castor oil; and polyglycerol fatty acid esters such as decaglycerine dioleate. Among the above, those with a molecular weight of 1000 or more are used. Further, the preferable molecular weight is 1500 or more, and thus particularly preferable are POE stearyl ether, POE oleyl ether, POE monostearate, POE monooleate, POE cholestanol ether, POE cholesterol ether, and POE hydrogenated castor oil derivatives.

The molecular weight of the nonionic surfactants is preferably 1000 or more. When the molecular weight is less than 1000, the stimulation or irritation to the organisms is strong and, when such nonionic surfactants are used as an injection liquid, hemolysis is likely to occur.

Also, the phospholipid and the water-soluble nonionic surfactant with a molecular weight of 1000 or more may be used alone or in any combination thereof. The use of the phospholipid in combination with the water-soluble nonionic surfactant is preferable. The preferable weight ratio of the phospholipid/the nonionic surfactant is 9.5/0.5 to 1/9, more preferably 1/9 to 2/8.

The particle size of the emulsified composition according to the present invention is 0.010 to 0.070 $\mu$m, preferably 0.050 $\mu$m or less, more preferably 0.040 $\mu$m or less.

The particle size of the emulsified composition in the present invention depends on the weight ratio of (A) and (C), and the particle size tends to become smaller as the (A)/(C) ratio is lowered. Therefore, if this ratio exceeds 5, an emulsified composition with an average particle size of 0.07 $\mu$m or less cannot be obtained, and to obtain an emulsified composition with an average particle size of 0.050 $\mu$m or less, which is the preferable particle size, the ratio must be 3 or less.

The administration of a large amount of a surfactant functioning as the emulsifier is not preferable, as it has an adverse affect on the blood system or blood. Accordingly, it is important to obtain small particles with as little an amount of a surfactant as possible, and therefore, the preferable ratio is 1.0 or more.

In the present invention, the weight ratio of (A)/(C) is 0.5 to 5, preferably 1.0 to 3.0.

In the present invention, the weight ratio of glycerol/water during emulsification is preferably 3/7 to 9/1, more preferably 1/1 to 8/2.

If the weight ratio of glycerol/water during emulsification is lower than 3/7, the effect of the addition thereof will not be exhibited, but if larger than 9/1, the expected effect of making the particle size smaller can not be obtained.

Although there are no critical limitation to the contents of the components (A), (B), and (C) in the present composition, the contents (A), (B), and (C) are preferably 1% to 40% by weight, 40% to 95% by weight, and 0.5% to 20% by weight.

The average particle size of the emulsified composition obtained by the present invention is 0.010 to 0.070 $\mu$m.

Also, in the present invention, by effecting the emulsification by an emulsifying machine capable of providing a strong shearing force, such as a high pressure homogenizer or sonication emulsifying machine, lipid spheres with particle sizes of 0.050 $\mu$m or less can be obtained.

For example, when preparing an emulsified composition with an (A)/(C) of 3, when emulsification is effected without an addition of glycerol, it is very difficult to obtain lipid spheres with particle sizes of 0.100 $\mu$m or less, even if the emulsification conditions of a high pressure homogenizer are variously changed, and impossible to obtain lipid spheres with particle sizes of 0.070 $\mu$m or less. When, however, emulsification is effected at a weight ratio of glycerol/water during emulsification of 3/7 to 9/1, lipid spheres with particle sizes of 0.050 $\mu$m or less can be obtained. Further, in the case of an (A)/(C) of 1, when glycerol is not used, it is very difficult to obtain lipid spheres with particles sizes of 0.070 $\mu$m or less, and impossible to obtain lipid spheres with particles sizes of 0.050 $\mu$m or less. When, however, emulsification is effected at a weight ratio of glycerol/water during emulsification of 3/7 to 9/1, lipid sphere with particle sizes of 0.020 $\mu$m or less can be obtained.

When a high pressure homogenizer is employed, preferably emulsification is effected under a pressure of 200 atm. or more, more preferably at a temperature of 70° C. or lower under a pressure of 300 atm. or higher when obtaining particles of 0.050 $\mu$m or less. To obtain smaller particles, the emulsification is preferably effected at a temperature of 50° C. or less under a pressure of 500 atm or more.

The emulsified composition can be diluted, by an addition of water, to a desired glycerol concentration before use. The glycerol concentration in the present invention is an isotonic concentration or more, although it may be varied depending upon the intended use thereof.

The emulsified composition of the present invention can also formulate, in addition to the essential components and various parenterally administratable components within the range which does not impair the effect of the present invention. As the aqueous phase components included among such components, are amino acids and related compounds, electrolytes, and water-soluble vitamins.

As explained above, whereas, only fine particles with an average particle size of a micro-order can be obtained in the prior art, stable ultra-fine particles of a nano-order can be obtained in the present invention.

Lipid nanospheres in such an emulsified composition, particularly those having particle sizes of 0.050 μm or less, when administered intravenously, intraarterially or intraperitoneally, are considered to pass through the reticuloendothelial system and accumulate at the tumor tissues, and the composition can be utilized as a novel and effective preparation for parenteral administration, and as a drug delivery system of as an antitumor agent etc.

As described in detail above, according to the present invention, an emulsified composition having stable lipid nanospheres with an average particle size of 0.010 to 0.070 μm dispersed in an aqueous phase can be obtained by formulating the lipid-soluble drug and the lipid, glycerol and water, the phospholipid and/or the water-soluble nonionic surfactant having a molecular-weight of 1000 or more.

EXAMPLES

The present invention will now be further illustrated by, but is by no means limited to, the following Examples, wherein all parts and percentages are expressed on a weight basis unless otherwise noted.

Correlation between (A)/(C) and Average Particle Diameter

First, the correlation between the weight ratio of the lipid-soluble drug and lipid to the phospholipid and/or water-soluble nonionic surfactant having a molecular weight of 1000 or more and the average particle diameter will now be explained.

The formulation during emulsification was adjusted as shown in Table 1 and treated 30 times in a high pressure homogenizer under an emulsification pressure of 900 atm. The average particle size of the resultant emulsified product was determined. The formulation amount listed in Table 1 is % by weight.

TABLE 1

| (A)/(C) Ratio | (A) | (C) | 60% Aqueous Glycerol Solution |
|---|---|---|---|
| 1 | 12 | 12 | 76 |
| 2 | 20 | 10 | 70 |
| 3 | 24 | 8 | 68 |
| 4 | 24 | 6 | 70 |
| 5 | 25 | 5 | 70 |
| 6 | 24 | 4 | 72 |
| 7 | 28 | 4 | 68 |

In FIG. 1, the correlation between (A)/(C) and the particle diameter when nonyloxycarbonyl mitomycin (NOC.MMC) 1% soybean oil solution was used as the component (A) (i.e., lipid-soluble drug and lipid) and yolk phosphatidylcholine was used as the component (C) (i.e., phospholipid). As is clear from FIG. 1, the (A)/(C) and the particle diameter are in approximate direct proportion and the particle diameter is 70 nm (0.070 μm) when the (A)/(C) is about 5, and the particle diameter becomes too large when the (A)/(C) is further increased.

From the results shown in FIG. 1, it is clear that the ratio of (A)/(C) is closely related to the particle diameter and that the desired particle diameter of 70 nm or less according to the present invention can be obtained when the ratio (A)/(C) is 5 or less. Furthermore, the particle diameter becomes smaller in approximate direct proportion to the ratio (A)/(C). Nevertheless, when the (A)/(C) is 3 or less, the linearity of the correlation between the (A)/(C) and the particle diameter is impaired and the particle diameter is not decreased in direct proportion to the decrease in the ratio (A)/(C). Accordingly, it is not efficient to decrease the particle diameter to 50 nm or less by using yolk phosphatidylcholine alone because a large amount of the yolk phosphatidylcholine must be used.

Figure 2:
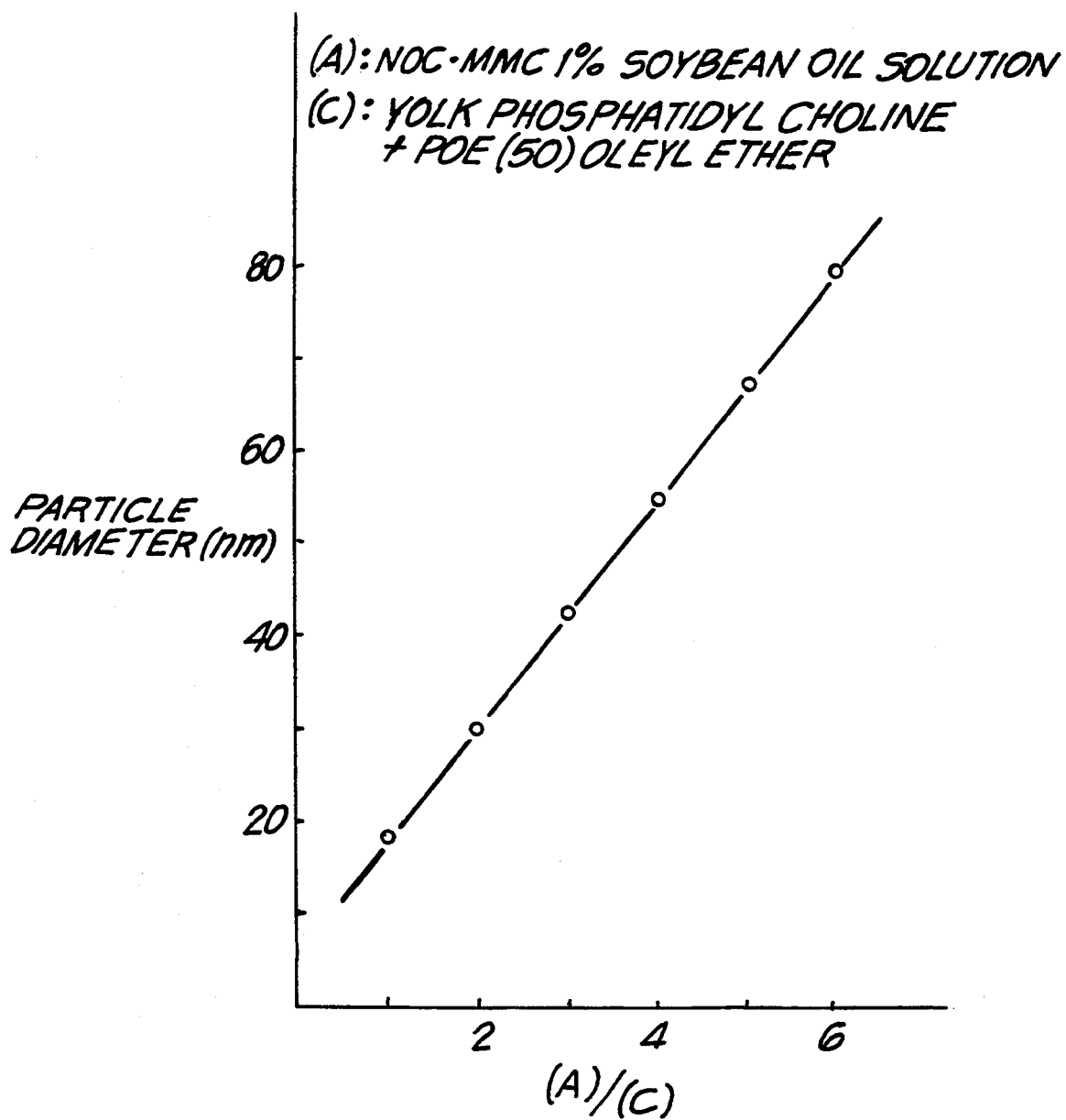
FIG. 2 shows a correlation between a particle diameter and a ratio (A)/(C) when a phospholipid and a nonionic surfactant are used as a component (C)

On the other hand, FIG. 2 shows the correlation between the (A)/(C) and the particle diameter when a 3:1 mixture of yolk phosphatidylcholine and POE (50) oleyl ether was used as the component (C). As is clear from the results shown in FIG. 2, a good linearity can be maintained even when the ratio (A)/(C) is 3 or less. Accordingly, when the preparation of particles having a diameter of 50 nm or less is desired, the use of a water-soluble nonionic surfactant having a molecular weight of 1000 or more, in addition to the phospholipid, is preferable.

Correlation between Ratio of Glycerol to Water and Particle Diameter

Next, the correlation between the ratio of glycerol to water and the particle diameter will now be explained.

A 20 parts amount of NOC.MMC 1% soybean oil solution, 10 parts of an emulsifier, and 70 parts of aqueous glycerol solution were formulated, followed by treating 30 times under an emulsification pressure of 600 atm in a high pressure homogenizer. Thus, the emulsified composition product was obtained.

The glycerol concentration of the above-mentioned aqueous glycerol solution were consecutively changed to determine the particle size of the resultant emulsified product.

Figure 3:
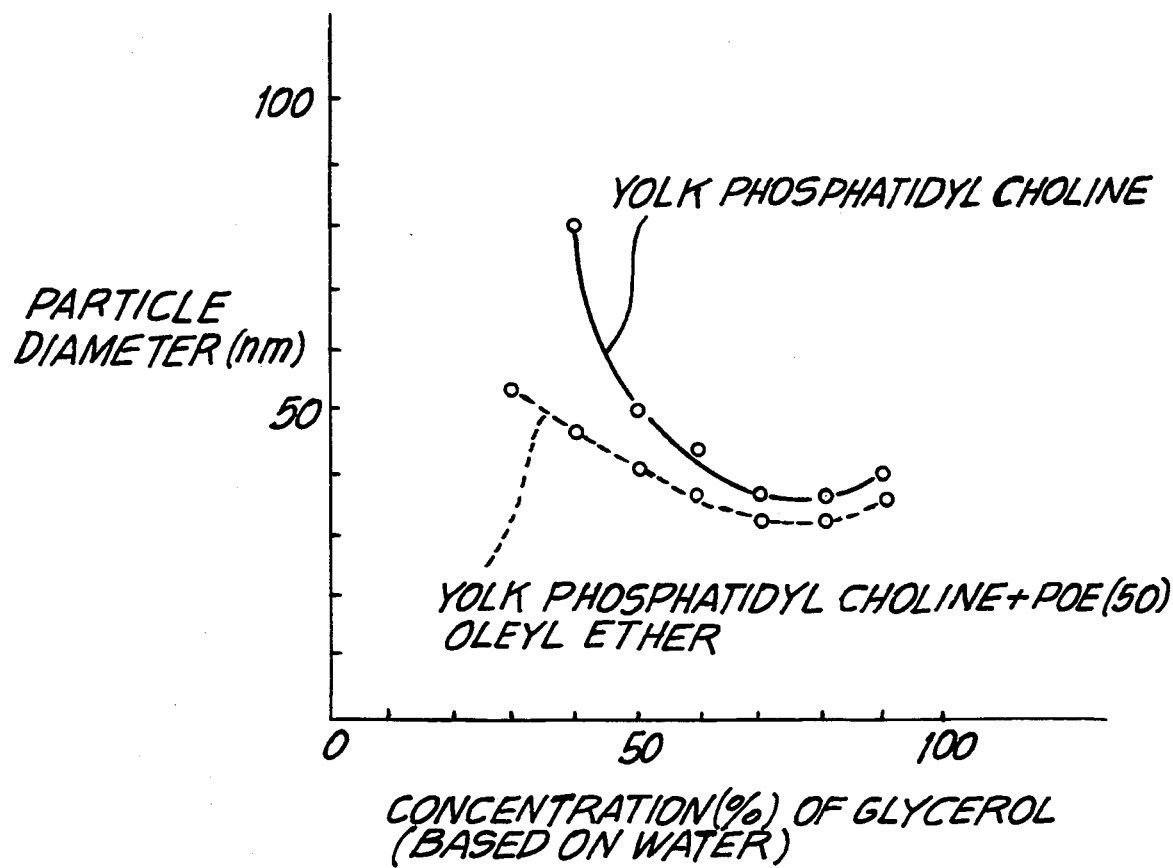
FIG. 3 shows a correlation between the concentration of glycerol and the particle diameter.

The results are shown in FIG. 3. As is clear from the results shown in FIG. 3, when yolk phosphatidylcholine was used as the emulsifier (see solid line in FIG. 3), the desired particle diameter of 70 nm or less was obtained at a glycerol concentration of 50% or more. Furthermore, the minimum particle diameter value was obtained at a glycerol concentration of 70 to 80%. When the glycerol concentration was decreased from the minimum point, the particle diameter became rapidly larger.

Further, when a 3:1 mixture of yolk phosphatidylcholine and POE (50) oleyl ether was used as the emulsifier (as shown in the dotted line in FIG. 3), the desired particle size of 70 nm or less was obtained at a glycerol concentration of 30% or more and the minimum particle diameter value was obtained at a glycerol concentration of 70 to 80%. Accordingly, the preferable glycerol concentration is 30 to 90% and, especially when the glycerol concentration is 70 to 80%, an extremely small particle diameter can be obtained.

Correlation between Ratio of Phospholipid and Nonionic Surfactant and Particle Diameter After preemulsifying 5.0% of tocopherol acetate, 15.0% of soybean oil, 10% of an emulsifier, 30% of water, and 40.0% of glycerol, the preemulsified product was treated 30 times at 50° C. under a pressure of 800 atm by using a Microfluidizer. Thus, the emulsified product was obtained.

The composition of the emulsifier and the particle diameter are shown in Table 2.

TABLE 2

| Lecithin:POE (50) stearyl ether | Particle Diameter (μm) |
|---|---|
| 1:0 | 0.040 |
| 0.9:0.1 | 0.034 |
| 0.75:0.25 | 0.032 |

TABLE 2-continued

| Lecithin:POE (50) stearyl ether | Particle Diameter (μm) |
| --- | --- |
| 0.5:0.5 | 0.032 |
| 0.25:0.75 | 0.035 |
| 0:1 | 0.044 |

As is clear from the results shown in Table 2, a finer particle size can be obtained by using a mixture of lecithin (i.e., phospholipid) and POE (50) stearyl ether (i.e., water-soluble nonionic surfactant having a molecular weight of 1000 or more), compared with the use of the lecithin or the POE (50) stearyl ether alone. Especially when the ratio of the lecithin is 75 to 50%, an extremely fine particle diameter can be obtained.

EXAMPLES 1-9

First, 1.1 parts of diclofenac, 20.9 parts of soybean oil, 28 parts of water, 41.3 parts of glycerol, and 8.7 parts of the phospholipid shown in Table 3 and/or the water-soluble nonionic surfactant having a molecular weight of 1000 or more (i.e., emulsifier) were preemulsified, then emulsification was effected at 50° C. by a Microfluidizer (Microfluidisc Co.) under the conditions of 1000 atm. and a 20 times treatment, and thereafter, 120 parts of water were added and the emulsion was sterilized by passing the same through a 0.22 μm membrane filter. The particle diameters of these emulsified compositions immediately after preparation are shown in Table 3. These particles are translucent or substantially transparent. As a result of an evaluation of the state and the particle diameter of the emulsions after standing at room temperature for 3 months, no change thereof was observed.

TABLE 3

| | Emulsifier | Particle diameter (μm) |
| --- | --- | --- |
| Example 1 | Purified yolk lecithin | 0.046 |
| Example 2 | Purified yolk lecithin + POE 60 hydrogenated castor oil derivative (8:2) | 0.040 |
| Example 3 | same as above (1:1) | 0.040 |
| Example 4 | same as above (3:7) | 0.045 |
| Example 5 | Hydrogenated castor oil derivative | 0.049 |
| Example 6 | Purified yolk lecithin + POE 30 cholestanol ether (1:1) | 0.038 |
| Example 7 | POE 30 cholestanol ether | 0.047 |
| Example 8 | Purified soybean lecithin | 0.047 |
| Example 9 | Decaglycerine dioleate | 0.050 |

COMPARATIVE EXAMPLES 1-9

The same compositions, except that the glycerine in the recipes shown in Examples 1-9 was replaced with water, were similarly prepared to give Comparative examples. The particle diameters of these emulsified compositions immediately after preparation are shown in Table 2. As a result of an evaluation of the state and the particle diameter of the emulsions after standing at room temperature for 3 months, no change thereof was observed.

TABLE 3

| | Emulsifier | Particle diameter (μm) |
| --- | --- | --- |
| Comparative Example 1 | Purified yolk lecithin | 0.101 |
| Comparative Example 2 | Purified yolk lecithin + POE 60 hydrogenated castor oil derivative (8:2) | 0.093 |
| Comparative Example 3 | same as above (1:1) | 0.098 |
| Comparative Example 4 | same as above (3:7) | 0.106 |
| Comparative Example 5 | Hydrogenated castor oil derivative | 0.117 |
| Comparative Example 6 | Purified yolk lecithin + POE 30 cholestanol ether (1:1) | 0.092 |
| Comparative Example 7 | POE 30 cholestanol ether | 0.099 |
| Comparative Example 8 | Purified soybean lecithin | 0.105 |
| Comparative Example 9 | Decaglycerine dioleate | 0.100 |

As shown in Table 3 and Table 4, the superiority of Examples 1-9 formulated with glycerol according to the present invention is obvious.

EXAMPLE 10

First, 15 parts of soybean oil containing 10% of 5-FU palmitate, 16 parts of water, 56 parts of glycerol, and 15 parts of POE 40 cholestanol ether were preemulsified, then emulsification was effected at 50° C. by Manton Gaulin under the conditions of 500 atm. and a 30 times treatment, and thereafter, 100 parts of water were added, and the emulsion was sterilized by passing the same through a 0.22 μm membrane filter and were transparent. As a result of an evaluation of the state and the particle diameter of the emulsions after standing at room temperature for 3 months, no change thereof was observed.

EXAMPLE 11

First, 20 parts of soybean oil containing 10% of 5-FU palmitate, 16 parts of water, 56 parts of glycerol, and 10 parts of POE (40) cholestanol ether were preemulsified, then emulsification was effected at 50° C. by Manthon Gaulin under the conditions of 500 atm. and a 30 times treatment, and thereafter, 100 parts of water were added and the emulsion was sterilized by passing the same through a 0.22 μm membrane filter. These emulsion compositions immediately after preparation had a particle diameter of 0.042 μm and were transparent. As a result of an evaluation of the state and the particle diameter of the emulsions after standing room temperature for 3 months, no change thereof was observed.

EXAMPLE 12

First 24 parts of soybean oil containing 10% of 5-FU palmitate, 16 parts of water, 54 parts of glycerol, and 8 parts of POE 40 cholestanol ether were preemulsified, then emulsification was effected at 50° C. by Manton Gaulin under the conditions of 500 atm. and a 30 times treatment, and thereafter, 100 parts of water were added and the emulsion was sterilized by passing the same through a 0.22 μm membrane filter. These emulsion compositions immediately after preparation had a particle diameter of 0.062 μm and were transparent. As a result of an evaluation of the state and the particle diameter of the emulsions after standing at room temperature for 3 months, no change thereof was recognized.

As shown in the results of Examples 10–12, according to the present invention, it is obvious that the particle diameter is controlled by the ratio of lipid to emulsifier.

EXAMPLE 13

First, 2 parts of futrafural palmitate, 1 part of soybean oil, 19 parts of ethyl oleate, 14 parts of water, 54 parts of glycerol, 5 parts of purified yolk lecithin, and 5 parts of POE 60 hydrogenated castor oil were preemulsified, then emulsification was effected at 50° C. by Manton Gaulin under the conditions of 500 atm. and a 10 times treatment, and thereafter, 100 parts of water were added and the emulsion was sterilized by passing the same through a 0.22 μm membrane filter.

These emulsion compositions immediately after preparation had a particle diameter of 0.028 μm and were transparent. As a result of an evaluation of the state and the particle diameter of the emulsions after standing at room temperature for 3 months, no change thereof was observed.

EXAMPLE 14

First, 1 part of cyclosporin, 1 part of soybean oil, 14 parts of ethyl laurate, 16 parts of water, 58 parts of glycerol, 7 parts of purified yolk lecithin, and 3 parts of POE (60) hydrogenated castor oil were preemulsified, then emulsification was effected at 50° C. by Manton Gaulin under the conditions of 500 atm. and a 10 times treatment, and thereafter, 100 parts of water were added and the emulsion was sterilized by passing the same through a 0.22 μm membrane filter. These emulsion compositions immediately after preparation had a particle diameter of 0.020 μm and were transparent. As a result of an evaluation of the state and the particle diameter of the emulsions after standing at room temperature for 3 months, no change thereof was observed.

EXAMPLE 15

First, 2 parts of erythromycin, 1 part of soybean oil, 27 parts of glycerine tricaprylate, 38 parts of water, 26 parts of glycerol, 1 part of purified yolk lecithin, and 6 parts of POE (30) cholestanol ether were preemulsified, then emulsification was effected at 70° C. by Microfluidizer (Microfluidisc Co.) under the conditions of 1000 atm. and a 20 times treatment, and thereafter, 100 parts of water were added and the emulsion was sterilized by passing the same through a 0.22 μm membrane filter. These emulsion compositions immediately after preparation had a particle diameter of 0.062 μm and were translucent. As a result of an evaluation of the state and the particle diameter of the emulsions after standing at room temperature for 3 months, no change thereof was observed.

EXAMPLE 16

First, 24 parts of soybean oil, containing 0.001% of prostaglandin $E_2$, 36 parts of water, 38 parts of glycerol, and 10 parts of POE (50) cholestanol ether were preemulsified, then emulsification was effected at 70° C. by Microfluidizer (Microfluidisc Co.) under the conditions of 1000 atm. and a 20 times treatment, and thereafter, 100 parts of water were added and the emulsion was sterilized by passing the same through a 0.22 μm membrane filter. These emulsion compositions immediately after preparation had a particle diameter of 0.047 μm and were translucent. As a result of an evaluation of the state and the particle diameter of the emulsions after standing at room temperature for 3 months, no change thereof was observed.

EXAMPLE 17

First, 25 parts of tocopherol acetate, 2 parts of soybean oil, 9 parts of purified yolk lecithin, 32 parts of water, and 32 parts of glycerol were preemulsified, then emulsification was effected at 50° C. by Manton Gaulin under the conditions of 500 atm. and a 20 times treatment, and thereafter, 100 parts of water were added and the emulsion was sterilized by passing the same through a 0.22 μm membrane filter. Further, 1050 parts of sterilized water were added thereto to obtain an isotonic liquid, i.e., vitamin E preparation for intravenous administration. The particle diameter of the preparation was 0.050 μm.

As a result of an evaluation of the state and the particle size of the emulsion after standing at room temperature for 3 months, no change thereof was observed.

EXAMPLE 18

First, 0.2 parts of nonyloxycarbonyl mitomycin, 19.8 parts soybean oil, 5 parts of yolk phosphatidyl choline, 5 parts of POE (50) monostearate, 30 parts of water, and 40 parts of glycerol were preemulsified, then emulsification was effected at 50° C. by Microfluidizer under the conditions of 800 atm. and a 30 times treatment, and thereafter, 100 parts of water were added and the emulsion was sterilized by passing the same through a 0.22 μm membrane filter. Further, 300 parts of sterilized water were added thereto to obtain nonyloxy carbonyl mitomycin C for intravenous administration. The particle diameter of the preparation was 0.32 μm.

As a result of an evaluation of the state and the particle size of the emulsion after standing at room temperature for 3 months, no change thereof was observed.

EXAMPLE 19

First, 0.1 part of amphotericin B, 9.9 parts of soybean oil, 8 parts of yolk phosphatidyl choline, 2 parts of POE (30) oleyl ether, 30 parts of water, and 50 parts of glycerol were preemulsified, then emulsification was effected at 40° C. by a Microfluidizer under the conditions of 800 atm. and a 30 times treatment, and thereafter, 100 parts by weight of water were added and the emulsion was sterilized by passing the same through a 0.22 μm membrane filter. Further, 100 parts of sterilized water were added and amphotericin B preparation for intravenous administration. The emulsified particle diameter was 0.018 μm.

As a result of an evaluation of the state and the particle size of the emulsion after standing at room temperature for 3 months, no change thereof was observed.

We claim:

1. An emulsified composition having an average particle size of 0.010 to 0.070 μm comprising at least the following components, (A), (B) and (C);

(A) at least one lipid selected from the group consisting of vegetable oils, synthetic and semi-synthetic mono-, di-, and tri-glycerides, sterols, cholesterol esters, and monoesters and at least one lipid-soluble drug, selected from the group consisting of antitumor agents, antibacterial and antifungal agents, non-steroidal antiphlogistics, hormone agents, and lipid-soluble vitamins, the content of the drug being $1 \times 10^{-6}\%$ to 99.9% by weight in the component (A);

(B) glycerol and water, the content of the glycerol being an isotonic concentration or more; and (C) at least one component selected from the group consisting of phospholipids and water-soluble nonionic surfactants having a molecular weight of 1000 or more, said phospholipids being selected from the group consisting of yolk lecithin, soybean lecithin and hydrogenated products thereof, phosphatidyl inositol, phosphatidylserine, sphingomyelin, phosphatidicacid, and phytoglycolipid, wherein the weight ratio of (A)/(C) is 0.5 to 5 and the weight ratio of (A)/(B)/(C) is 1–40/40–95/0.5–20, said emulsified composition being emulsified by using a mixture of glycerol and water at a weight ratio of glycerol/water during emulsification of 3/7 to 9/1.

2. An emulsified composition as claimed in claim 1, wherein the weight ratio of glycerol/water in the component (B) during emulsification is 3/7 to 9/1.

3. An emulsified composition as claimed in claim 1, wherein said component (C) comprises at least one phospholid and at least one water-soluble nonionic surfactant in a weight ratio of 9.5/0.5 to 1/9.

4. An emulsified composition as claimed in claim 1, wherein the contents of the components (A), (B), and (C) are 1 to 40% by weight, 40% to 95% by weight, and 0.5 to 20% by weight, respectively, based on the total weight of the composition.

5. An emulsified composition as claimed in claim 1, wherein the weight ratio of (A)/(C) is 0.5 to 3.

6. An emulsified composition as claimed in claim 1, wherein the average particle size is 0.01 to 0.05 μm.

* * * * *